United States Patent [19]
Maclean et al.

[11] Patent Number: 6,100,301
[45] Date of Patent: Aug. 8, 2000

[54] COMBINATION THERAPY TO TREAT OSTEOPOROSIS-POLYPHOSPHONATES AND ESTROGEN AGONISTS

[75] Inventors: David B. Maclean, Providence, R.I.; David D. Thompson, Gales Ferry, Conn.

[73] Assignee: Pfizer Inc, New York, N.Y.

[21] Appl. No.: 09/092,100

[22] Filed: Jun. 5, 1998

Related U.S. Application Data

[60] Provisional application No. 60/012,409, Feb. 28, 1996.

[51] Int. Cl.[7] .......................... A61K 31/135; A61K 38/00
[52] U.S. Cl. .............................................. 514/648; 514/12
[58] Field of Search ........................ 514/648, 12

[56] References Cited

U.S. PATENT DOCUMENTS

| | | | |
|---|---|---|---|
| 5,118,886 | 6/1992 | Adam et al. ............................. | 514/12 |
| 5,462,932 | 10/1995 | Brenner et al. ......................... | 514/108 |

FOREIGN PATENT DOCUMENTS

| | | | |
|---|---|---|---|
| 3804686 | 2/1988 | Germany ....................... | A61K 31/66 |
| 94144456 | 7/1994 | WIPO ............................. | A61K 31/66 |

*Primary Examiner*—Jerome D. Goldberg
*Attorney, Agent, or Firm*—Peter C. Richardson; Paul H. Ginsburg; Elsa Djuardi

[57] ABSTRACT

The present invention provides novel methods of treating or preventing osteoporosis comprising administering to a mammal in need of such treatment an effective amount of a compound of formula I (I)

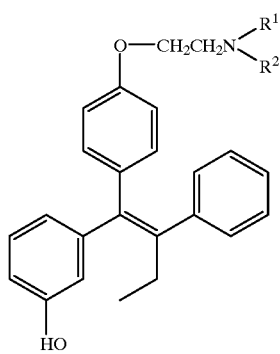

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with a bone resorption inhibiting polyphosphonate, or with parathyroid hormone.

9 Claims, No Drawings

COMBINATION THERAPY TO TREAT OSTEOPOROSIS-POLYPHOSPHONATES AND ESTROGEN AGONISTS

This application is a division of Application No. 08/803,707, filed Feb. 21, 1997, which issued U.S. Pat. No. 5,773,477 on June 30, 1998, which claims the benefit of U.S. Provisional No. 60/012,409, filed on Feb. 28, 1996.

BACKGROUND OF THE INVENTION

Osteoporosis describes a group of diseases which arise from diverse etiologies, but which are characterized by the net loss of bone mass per unit volume. A consequence of this loss of bone mass is the failure of the skeletal frame to provide adequate structural support for the body, resulting in bone fracture. One of the most common types of osteoporosis occurs in women shortly after menopause. Most women lose between 20–60% of the bone mass in the trabecular compartment of the bone within 3–6 years after the cessation of menses. This rapid loss of bone mass is generally associated with an increase of both bone resorption and formation. The resorptive cycle is more dominant, however; and the result is a net loss of bone mass.

Thus, ostecporosis is a common and serious disease among post-menopausal women. An estimated 25 million women in the United States alone are afflicted with this disease. The results of this disease are both personally and economically harmful. Large economic losses are due to its chronic nature and the need for extensive and long term support (hospitalization and nursing home care) from the disease sequelae. The losses are especially great in more elderly patients. Additionally, although osteoporosis is not generally considered a life threatening condition, there is a 20–30% mortality rate related to hip fractures in elderly women. A large percentage of this mortality rate can be directly associated with post-menopausal osteoporosis.

The tissue in the bone most vulnerable to the effects of post-menopausal osteoporosis is the trabecular bone. This tissue is often referred to as spongy or cancellous bone and particularly concentrated near the ends of the bone, near the joints and in the vertebrae of the spine. Trabecular tissue is characterized by small osteoid structures which interconnect with each other and with the more solid and dense cortical tissue that makes up the outer surface and central shaft of the bone. This criss-cross network of trabeculae gives lateral support to the outer cortical structure and is critical to the bio-mechanical strength of the overall structure. It is primarily the net resorption and loss of the trabeculae which leads to the failure and fracture of bone in post-menopausal osteoporosis. In light of the loss of the trabeculae in post-menopausal women, it is not surprising that the most common fractures are those associated with bones which are highly dependent on trabecular support, e.g., the vertebrae, the neck of the weight bearing bones (femur) and the forearm. Indeed, hip fracture, collies fractures, and vertebral crush fractures are hall-marks of post-menopausal osteoporosis.

A very important concept in the treatment and study of post-menopausal osteoporosis is the concept of fracture threshold. The fracture threshold is the point at which the bone density (therefore, the bone strength) decreases to a value where there is a high probability of bone fracture. This point is not a particular value for all women but rather a relative number for an individual and is dependent on a number of factors such as weight, life-style, or other risks which might contribute to the possibility of bone fracture.

In general, most pre-menopausal women have bone densities above the fracture threshold, and there is a low probability that a fracture will occur. A woman's pre-menopausal bone density and the rate of bone loss after menopause will determine when, or if, she will cross the threshold and be at risk for fracture. For women who present with fractures due to osteoporosis, ideal therapy would be to increase bone density (strength) to a value above the fracture threshold. Alternatively, for women whose bone density is still above the threshold, it would be advantageous to keep them above it.

Today, the only available effective treatment for post-menopausal osteoporosis is hormone replacement therapy, specifically estrogen replacement because post-menopausal women are estrogen deficient The mechanism of action of estrogen in the treatment of osteoporosis is not well understood; however, it is generally agreed that it inhibits bone resorption. The net effect of the estrogen replacement therapy (ERT) is to keep the woman's bone density at the level at which therapy was initiated, i.e., it maintains bone density. If a woman is above the fracture threshold when (ERT) is initiated, and if ERT is maintained, she will remain above the threshold and be at low risk for fracture. This fact would argue for the placement of women on ERT at or soon after the cessation of menses.

For women whose bone density has already fallen below the fracture threshold, however, ERT will only maintain bone density at the level at which they began therapy. Thus, these women will remain below the threshold and will be at further risk for fracture. ERT is still advisable for these women because it will keep a bad situation from getting worse. It would clearly be advantageous, however, to have a therapy which would boost bone density above the fracture threshold to more normal levels and then maintain it Currently, there are no effective approved therapies which demonstrate an ability to increase bone density to such a level.

As noted, ERT is now the only effective approved treatment for post-menopausal osteoporosis. In those women who do not have a uterus, estrogen (usually given as a conjugated form of estrone) can be given by itself. In most post-menopausal women who have a uterus, however, unopposed estrogen increases the risk of endometrial cancer. Thus, a progestin is often also administered, either as a combination or in cyclical therapy, to reduce that risk.

"Antiestrogen" is a term that "has been rather broadly applied to several different types of compounds that inhibit or modify the action of estrogen. Progestins and androgens have been described as antestrongenic . . ." (Goodman and Gilman, *The Pharmacological Basis of Therapeutics*, 6th Ed., p 1431.) In addition, certain synthetic compounds, such as tamoxifene, clomiphene, droloxifene and nafoxidine, are called antiestrogens and have been shown both experimentally and clinically to block some of the effects of estrogen. The synthetic "antiestrogens" were principally developed for the treatment of estrogen-dependent breast carcinoma. These compounds are classical mixed agonist/antagonists which demonstrate some estrogenic activity. For example, tamoxifene, the most widely used antiestrogen, has been shown to have estrogenic effects in humans.

The combination of certain 3-benzoyl-benzothiophenes and a progestin has been found to be effective in preventing bone loss. EP 665,015 A2.

European patent EP 0381296 A1 describes the use of a bone cell activating compound in combination with a bone resorption inhibiting polyphosphonate for treatment or prevention of osteoporosis.

Adams et al., U.S. Pat. No. 5,118,667, disclose the use of bone growth factors in combination with bone resorption inhibitors, either simultaneously in one composition or sequentially, to promote bone formation.

U.S. Pat. No. 5,254,594 claims the use of droloxifene and related compounds to prevent bone loss.

Slovik et al. (J. Bone & Min. Res. 1:377–381, 1986) report the stimulation of bone growth by parathyroid hormone (PTH).

Raloxifene is described in U.S. Pat. No. 4,418,068; in EP-A-584952 it is disclosed that raloxifene is useful in inhibition or prevention of bone loss and in EP-A1-635270 that it is useful in combination with parathyroid hormone to prevent bone loss.

SUMMARY OF THE INVENTION

The present invention relates to methods for treating or preventing osteoporosis comprising administering to a mammal in need of such treatment an effective amount of a compound of formula I

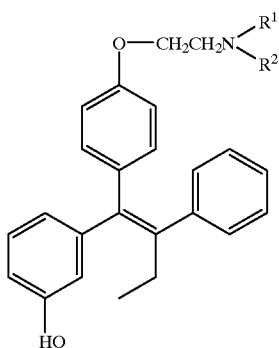

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with a bone resorption inhibiting polyphosphonate. A preferred compound of formula I is that in which $R^1$ and $R^2$ are methyl. A preferred salt is the citrate salt. Alendronate is a preferred polyphosphonate.

In another aspect, the present invention relates to methods for treating or preventing osteoporosis and other conditions which present low bone mass comprising administering to a mammal in need of such treatment an effective amount of a compound of formula I wherein $R^1$ and R2 may be the same or different provided that, when $R^1$ and $R^2$ are the same, each is a methyl or ethyl group, and, when $R^1$ and $R^2$ are different, one of them is a methyl or ethyl group and the other is a benzyl group, or a pharmaceutically acceptable salt thereof; together with or in combination with parathyroid hormone. A preferred compound of formula I is that in which $R_1$ and $R^2$ are methyl. A preferred salt is the citrate salt.

A preferred aspect of this method is wherein the condition which presents with low bone mass is osteoporosis.

Another preferred aspect of this method is wherein a compound of formula I and parathyroid hormone are administered substantially simultaneously.

Another preferred aspect of this method is wherein parathyroid hormone is administered for a period of from about three months to about three years.

Optionally the administration of parathyroid hormone is followed by administration of a compound of formula I for a period of from about three months to about three years without the administration of parathyroid hormone during the second period of from about three months to about three years.

Alternatively, the administration of parathyroid hormone is followed by administration of a compound of formula I for a period greater than about three years without the administration of parathyroid hormone during the greater than about three year period.

In another aspect this invention relates to a kit containing a treatment for a condition which presents low bone mass comprising:

a therapeutically effective amount of a compound of formula I and a pharmaceutically acceptable carrier in a first unit dosage form;

a therapeutically effective amount of parathyroid hormone and a pharmaceutically acceptable carrier in a second unit dosage form; and container means for containing said first and second dosage forms.

DETAILED DESCRIPTION OF THE INVENTION

The present invention concerns methods for inhibiting bone loss, including treatment and prevention of osteoporosis. The term "inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

The methods of this invention are practiced by administering to an individual in need of treatment an effective amount of a compound formula I

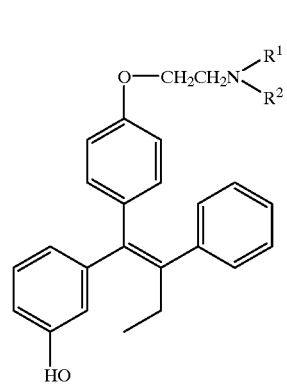

(I)

Wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with a bone resorption inhibiting polyphosphonate; or in combination with parathyroid hormone.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene (Formula I wherein $R^1$ and $R^2$ are methyl) which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

By "bone resorption inhibiting polyphosphonate" as used herein is meant a polyphosphonate of the type disclosed in U.S. Pat. No. 3,683,080, granted Aug. 8, 1972, the disclosures of which are incorporated herein by reference. Preferred polyphosphonates are geminal diphosphonates (also referred to as bis-phosphonates.) The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3amino-1-hydroxy-1,1-diphosphonic acid, propane-3-3-dimethyl-3amino-1-hydroxy-1,1-diphosphonic acid, phenyl amino methane diphosphonic acid,N,N-dimethylamino methane diphosphonic acid, N(2-hyroxyethyl) amino methane diphosphonic acid, butane4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

The amount of the polyphosphonate to be used is determined entirely by its potency as a bone resorption inhibiting agent. This potency is determined by means of the thyroparathyroidectomized (TPTX) rat model described herein and expressed as the lowest effective dose (LED) of the compound which is defined as the lowest subcutaneously given dose of polyphosphonate, in mg P per kg body weight, which in the TPTX rat model results in an inhibition of the PTH-induced rise in serum calcium level. Since the amount of polyphosphonate to be administered is dependent on the bone resorption inhibition potency of the compound, the amount to be administered is conveniently expressed as multiples of LED. Extrapolation of the dosages for polyphosphonates from the TPTX rat model to humans is possible based on the observation that oral dosages in humans are proportionally related to the LEDs for polyphosphonates in the TPTX rat model. It is therefore observed that suitable amounts of polyphosphonates for administration in subjects afflicted with or at risk to osteoporosis are from about 0.25 x LED to about 3.3 x LED, while amounts of from about 0.25 x LED to about 2.5 x LED are preferred, and amounts of from 0.50 x LED to 2.0 x LED are most preferred.

Ranges for the daily administration of some polyphosphonates for subjects afflicted with or at risk to osteoporosis are: ethane-1-hydroxy-1,1-diphosphonic acid: from about 0.25 mg P/kg to about 3.3 mg P/kg, with from about 0.25 mg P/kg to about 2.5 mg P/kg preferred; dichloromethane diphosphonic acid: from about 0.12 mg P/kg to about 1.67 mg P/kg, with from about 0.12 mg P/kg to about 1.25 mg P/kg preferred; propane-3-amino-1-hydroxy-1,1-diphosphonic acid: from about 0.025 mg P/kg to about 0.33 mg P/kg with from about 0.025 mg P/kg to about 0.25 mg P/kg preferred; butane4-amino-1-hydroxy-1,1-diphosphonic acid: from about 0.0025 mg P/kg to about 0.033 mg P/kg, with from about 0.0025 mg P/kg to about 0.025 mg P/kg preferred; and hexane-6-amino-1-hydroxy-1,1-diphosphonic acid: from about 0.025 mg P/kg to about 0.33 mg P/kg, with from about 0.025 mg P/kg to about 0.25 mg P/kg preferred.

The ranges of daily doses of the above polyphosphonates for use in the present invention are therefore (assuming that the majority of subjects afflicted with or at risk to osteoporosis weigh between about 10 kg and about 100 kg): ethane-1-hydroxy-1,1-diphosphonic acid: from about 2.5 mg P to about 330 mg P, with from about 2.5 mg P to about 250 mg P preferred, from about 15 mg P to about 200 mg P more preferred, and from about 15 mg P to about 150 mg P most preferred; dichloromethane diphosphonic acid: from about 1.2 mg P to about 167 mg P, with from about 1.2 mg P to about 125 mg P preferred, from about 7 mg P to about 100 mg P more preferred, and from about 7 mg P to about 75 mg P most preferred: propane-3-amino-1-hydroxy-1,1- diphosphonic acid: from about 0.25 mg P to about 33 mg P, with from about 0.25 mg P to about 25 mg P preferred, from about 1.5 mg P to about 20 mg P more preferred, and from about 1.5 mg P to about 15 mg P most preferred; butane4-amino-1-hydroxy-1,1-diphosphonic acid: from about 0.025 mg P to about 3.3 mg P, with from about 0.025 mg P to about 2.5 mg P preferred, from about 0.15 mg P to about 2.0 mg P more preferred, and from about 0.15 mg P to about 1.5 mg P most preferred; and hexane-6-amino-1-hydroxy-1.1-diphosphonic acid: from about 0.25 mg P to about 33 mg P, with from about 0.25 mg P to about 25 mg P preferred, from about 1.5 mg P to about 20 mg P more preferred, and from about 1.5 mg P to about 15 mg P most preferred.

Once prepared, the free base or salt form of formula I compounds together with a bone resorption inhibiting polyphosphonate can be administered to an individual in need of treatment for the methods herein described. The following nonlimiting test examples illustrate the methods of the present invention.

For the methods of the present invention, compounds of Formula I are administered continuously, or from 1 to 4 times daily together with a bone resorption inhibiting polyphosphonate.

As used herein, the term "effective amount" means an amount of compounds of the methods of the present invention which is capable of inhibiting the symptoms of the pathological conditions herein described. The specific dose of the compounds administered according to this invention will, of course, be determined by the particular circumstances surrounding the case including, for example, the compounds administered, the route of administration, the state of being of the patient, and the severity of the pathological condition being treated. For the combination of a compound of Formula I and polyphosphonate a typical daily dose will contain a nontoxic dosage level of from about 0.25 mg to about 100 mg/day of the compounds of the present invention. Preferred daily doses generally will be from about 1 mg to about 40 mg/day.

For the combination of a compound of Formula I and PTH a typical daily dose will contain a nontoxic dosage level of from about 0.25 mg to about 100 mg/day of a compound of formula I and about 0.01 mg to 70 mg PTH. Preferred daily doses generally will be from about 1 mg to about 40 mg/day of a compound of formula I and 1 to 40 mg of PTH.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, and a bone resorption inhibiting polyphosphonate are combined with a pharmaceutically acceptable carrier, diluent or excipient to form a pharmaceutical formulation.

The total active ingredients in such formulations comprises from 0.1% to 99.9% by weight of the formulation. By "pharmaceutcally acceptable" it is meant the carrier, diluent, excipients, and/or salt must be compatible with the other ingredients of the formulation, and not deleterious to the recipient thereof.

Pharmaceutical formulations containing a compound of formula I and a bone resorption inhibiting polyphosphonate can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof and a polyphoshonate or parathyroid hormone.

Formulation 1: Gelatin Capsules
Hard gelatin capsules are prepared using the following:

| Ingredient | Quantity (mg/capsule) |
| --- | --- |
| Active ingredients | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredients | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredients | 0.25–100 |
| Starch | 45 |

-continued

Formulation 3: Tablets

| Ingredient | Quantity (mg/tablet) |
|---|---|
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicaments per 5 ml dose are made as follows:

Formulation 4: Suspensions

| Ingredient | Quantity (mg/5 ml) |
|---|---|
| Active ingredients | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicaments are passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredients | 0.25 |
| Ethanol | 25.75 |
| Propellant 22 (Chlorodifluoromethane) | 70.00 |

The active ingredients are mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredients | 250 |
| Saturated fatty acid glycerides | 2,000 |

The active ingredients are passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
|---|---|
| Active ingredients | 20 mg |
| Isotonic saline | 1,000 mL |

The solution of the above ingredients is intravenously administered to a patient at a rate of about 1 mL per minute.

When a compound of formula I is referred to, it is understood that it includes salts and solvates thereof. When PTH is referred to, it not only includes the complete human hormone but also includes portions which include the portion of the hormone responsible for bone growth promotion, such as PTH 1-34, and analogs in which the amino acid sequence is modified slightly however, still retaining bone growth promotion properties, such as PTH-RP.

The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism.

The term "osteogenically effective" means that amount which effects the formation and differentiation of bone. As use herein, an osteogenically effective dose is also "pharmaceutically effective."

The term "subject" as used herein refers to a living vertebrate animal such as a mammal or bird in need of treatment, i.e., in need of bone repair or replacement. Such need arises locally in cases of bone fracture, non-union, defect, prosthesis implantation, and the like. Such need also arises in cases of systemic bone disease, as in osteoporosis, osteoarthritis, Paget's disease, osteomalacia, osteohalisteresis, multiple myeloma and other forms of cancer, and age-related loss of bone mass.

The term "treatment" as used herein shall mean (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

Any parathyroid hormone (PTH) may be used as the second compound of this invention. The term parathyroid hormone refers to parathyroid hormone, fragments or metabolites thereof and structural analogs thereof which can stimulate bone formation and increase bone mass. Such functional activity is readily determined by those skilled in the art according to standard assays (e.g., see Anabolic Agent Protocol described hereinafter and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1) :50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below however other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int. 1:162–170.

PTH 1-34 may be purchased from Bachem of Torrence, Calif.

Drugs which prevent bone loss, and/or add back lost bone and/or increase bone mass may be evaluated in the ovariectomized rat. This animal model is well established in the art (see, for example, Wronski, et al. (1985) Calcif. Tissue Int 37:324–328; Kimmel, et al. (1990) Calcif Tissue Int 46:101–110; and Durbridge, et al. (1990) Calcif. Tissue Int. 47:383–387; these references were hereby incorporated in their entirety). Wronski, et al. ((1985) Calcif. Tissue lnt. 43:179–183)) describe the association of bone loss and bone turnover in the ovariectomized rat Also, Hock et al., describe the use of immature rats ((1988) Endocrinology, Vol. 122, pp. 2899–2904).

PTH and a compound of formula 1 may be administered sequentially, concurrently, or simultaneously as a single composition to the subject. If administered sequentially, the period between the administration of PTH and a compound of formula I will typically be one week to one year, and optimally, one week to six months. In a preferred administration scheme, the subject will, after administration of PTH, with or without a compound of formula 1, be administered a compound of formula I after cessation of administration of PTH.

Pharmaceutical formulations of the invention which include PTH and/or a compound of formula I for administration will generally include an osteogenically effective amount of the bone growth factor to promote bone growth, in addition to a pharmaceutically acceptable excipient. Suitable excipients include most carriers approved for parenteral administration, including water, saline, Ringer's solution, Hank's solution, and solutions of glucose, lactose dextrose, ethanol, glycerol, albumin, and the like. These compositions may optically include stabilizers, antioxidants, antimicrobials, preservatives, buffering agents, surfactants, and other accessory additives. PTH and/or raloxifene may also be delivered in an iontophoretic patch. A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

If the combination is administered as a single composition, the molar ratio of PTH to a compound of formula I will be about 10:1 to 1:10, preferably, 5:1 to 1:5, and optimally, 1:1. Furthermore, if administered as a single composition, it may be separate components of the composition, or they may be conjugated to each other.

The precise dosage necessary will vary with the age, size, sex and condition of the subject, the nature and severity of the disorder to be treated, and the like; thus, a precise effective amount cannot be specified in advance and will be determined by the care giver. However, appropriate amounts may be determined by routine experimentation with animal models. In general terms, an effective dose of PTH for systemic treatment will range from about 0.001 mg/kg to about 10 mg/kg of body weight, per day. As effective dose for a compound of formula I is about 10 mg to 40 mg per day.

The methods and compositions of the invention are useful for treating bone fractures, defects, and disorders which result in weakened bones such as osteoporosis, osteoarthritis, Paget's disease, osteohalisteresis, osteomalacia, bone loss resulting from multiple myeloma and other forms of cancer, bone loss resulting from side effects of other medical treatment (such as steroids), and age-related loss of bone mass.

In accordance with one method of use, PTH and a compound of formula I may be administered systemically, orally and/or parenterally, including subcutaneous or intravenous injection, and/or intranasally.

In accordance with another method of use PTH may be administered locally to a specific area in need of bone growth or repair, with the concomitant administration of raloxifene at the site, or the administration of a compound of formula I in a separate vehicle, or, it may be provided locally, with the administration of PTH in a separate vehicle. Thus, the PTH and/or a compound of formula I may be implanted directly at the site to be treated, for example, by injection or surgical implantation. Suitable carriers include hydrogels, controlled- or sustained-release devices (e.g., an Alzet® minipump), polyactic acid, and collagen matrices. Presently preferred carriers are formulations of atelopeptide collagen containing particulate calcium phosphate mineral components, such as combinations of homologous or xenographic fibrillar atelopeptide collagen (for example Zyderm® Collagen Implant, available from Collagen Corporation, Palo Alto, Calif.) with hydroxyapatitetricalcium phosphate (HA-TCP, available from Zimmer, Inc., Warsaw, Ind.).

Dental and orthopedic implants can be coated with PTH in combination with raloxifene, to enhance attachment of the implant device to the bone. Alternatively, PTH can be used to coat the implant, and raloxifene can be administered concomitantly or sequentially in a separate vehicle, and vice versa.

In general, implant devices may be coated with a PTH and/or a compound of formula I as follows. The PTH (and compound of formula 1, if desired) is dissolved at a concentration in the range of 0.01 mg/ml to 200 mg/ml in phosphate-buffered saline (PBS) containing 2 mg/ml serum albumin. The porous end of an implant is dipped in the solution and is air dried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing PTH (and a compound of formula 1, if desired) is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is air-dried and rehydrated with PBS prior to implanting, with the objective of maximizing new bone formation into the implant while minimizing the ingrowth of soft tissue into the implant site.

EXAMPLE 1

In this example, a model of post-menopausal osteoporosis is used in which effects of different treatments upon femur density are determined.

Seventy-five day old female Sprague Dawley rats (weight range of 225 to 275 g) are obtained from Charles River Laboratories (Portage, Mich.). They are housed in groups of 3 and have ad libitum access to food (calcium content approximately 1%) and water. Room temperature is maintained at 22.2°±1.7° C. with a minimum relative humidity of 40%. The photoperiod in the room is 12 hours light and 12 hours dark.

One week after arrival, the rats undergo bilateral ovariectomy under anesthesia (44 mg/kg Ketamine and 5 mg/kg Xylazine (Butler, Indianapolis, Ind.) administered intramuscularly). Treatment with vehicle or the test compositions is initiated either on the day of surgery following recovery from anesthesia or 35 days following the surgery.

Oral dosage is by gavage in 0.5 mL of 1% carboxymethylcellulose (CMC).

Body weight is determined at the time of surgery and weekly during the study, and the dosage is adjusted with changes in body weight. Vehicle-treated ovariectomized (ovex) rats and non-ovariectomized (intact) rats are evaluated in parallel with each experimental group to serve as negative and positive controls.

The rats are treated daily for 35 days (6 rats per treatment group) and sacrificed by decapitation on the 36th day. The 35-day time period is sufficient to allow maximal reduction in bone density, measured as described infra. At the time of sacrifice, the uteri are removed, dissected free of extraneous issue, and the fluid contents were expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and scanned at the distal metaphysis 1 mm from the patellar groove with single photon absorptiometry. Results of the densitometer measurements represent a calculation of bone density as a function of the bone mineral content and bone width.

EXAMPLE 2

Rats are ovariectomized (OVX) 4 weeks of age and given sc vehicle (v) or hPTH 1-34 (P) at 8 mg/100 g/d alone or in combination with sc compound of formula I (C) at 0.3 mg/100 g/d as follows: V 24d; C 24d; P 24d; P&C 24d; P 12d then V12d; P 12d the C 12d; V12d; the C 12d. Rats are killed on d24, and blood, femurs, lumbar vertebrae and kidneys collected. Bone mass is measured as Ca and dry weight (DW) of distal half femurs; vertebrae are processed for histomorphometry.

Data are corrected per 100 g body weight. Distal half femur Ca and DW decrease in OVX compared to sham rats. Bone mass is increased by the compounds of formula I and by PTH.

What is claimed is:

1. A method for inhibiting conditions which present low bone mass comprising administering to a mammal in need of such inhibition an enhanced effective amount of a compound of formula I

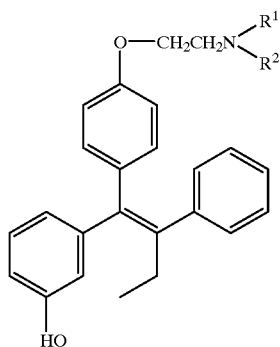

(I)

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen or a benzyl group; or a pharmaceutically acceptable salt thereof; together with or in combination with parathyroid hormone.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

4. A method as recited in claim 1 wherein the condition which presents with low bone mass is osteoporosis.

5. A method as recited in claim 1 wherein the compound of formula I and parathyroid hormone are administered substantially simultaneously.

6. A method as recited in claim 1 wherein parathyroid hormone is administered for a period of from about three months to about three years.

7. A method as recited in claim 6 followed by administration of a compound of formula I for a period of from about three months to about three years without the administration of parathyroid hormone during the period of from about three months to about three years.

8. A method as recited in claim 6 followed by administration of a compound of formula I for a period greater than about three years without the administration of parathyroid hormone during the greater than about three year period.

9. A pharmaceutical composition comprising an enhanced effective amounts of a compound of formula 1 as defined in claim 5 and parathyroid hormone.

* * * * *